(12) United States Patent
Yeh (10) Patent No.: US 12,285,353 B2
(45) Date of Patent: Apr. 29, 2025

(54) OPERATING METHOD OF AN ANTI-SNORING REHABILITATION DEVICE

(71) Applicant: Hong-Jun Yeh, Taichung (TW)

(72) Inventor: Hong-Jun Yeh, Taichung (TW)

( * ) Notice: Subject to any disclaimer, the term of this patent is extended or adjusted under 35 U.S.C. 154(b) by 426 days.

(21) Appl. No.: 17/901,838

(22) Filed: Sep. 1, 2022

(65) Prior Publication Data

US 2024/0074892 A1 Mar. 7, 2024

(51) Int. Cl.
| | |
|---|---|
| *A61F 5/56* | (2006.01) |
| *A61G 7/005* | (2006.01) |
| *A61G 7/015* | (2006.01) |
| *A61G 7/018* | (2006.01) |

(52) U.S. Cl.
CPC ........... *A61F 5/56* (2013.01); *A61G 7/005* (2013.01); *A61G 7/015* (2013.01); *A61G 7/018* (2013.01)

(58) Field of Classification Search
CPC .......... A61M 21/00; A61M 2021/0022; A47C 21/006; A61F 5/56; A61G 7/018; A61G 7/015; A61G 7/005; A61B 2562/0204; A47D 9/057; A47D 9/02; A61H 23/0254; A47G 2200/146

USPC ............... 601/98, 99, 100; 600/26
See application file for complete search history.

(56) References Cited

U.S. PATENT DOCUMENTS

| | | | | |
|---|---|---|---|---|
| 6,682,495 | B2* | 1/2004 | Park ............ | A47C 21/006 601/84 |
| 8,410,942 | B2* | 4/2013 | Chacon ............ | A61F 5/56 340/573.7 |
| 10,912,669 | B2* | 2/2021 | Shan ............ | A61B 5/4809 |
| 2012/0324649 | A1* | 12/2012 | Lin ............ | A61F 5/56 5/613 |
| 2015/0128347 | A1* | 5/2015 | Hutchison ............ | A61G 7/018 5/616 |
| 2019/0223612 | A1* | 7/2019 | Wattereson ............ | A47C 21/006 |

\* cited by examiner

*Primary Examiner* — David R Hare
*Assistant Examiner* — George Samuel Gines (57) ABSTRACT

An operating method of an anti-snoring rehabilitation device is provided. The method includes a starting step, a lifting step, a horizontal reciprocating step and an adjusting step. The anti-snoring rehabilitation device includes a detecting unit detecting the patient's snoring volume, time period, frequency, etc., and transmitting a control signal to a control substrate of an electric control screen for controlling a movable framework to lift, fold and horizontal reciprocate, so as to improve the user snoring.

4 Claims, 11 Drawing Sheets

OPERATING METHOD OF AN ANTI-SNORING REHABILITATION DEVICE

FIELD OF THE DISCLOSURE

The present disclosure is related to an operating method of an anti-snoring rehabilitation device, in particular, the technology used in the medical field.

BACKGROUND OF THE DISCLOSURE

Snoring is a disease also known as sleep apnea. II is mainly because the muscles of the respiratory tract, such as the tongue and soft palate being relaxed during sleep, and vibrated when the airflow passes through, so that the sound of snoring occurs. Snoring can be sporadic or recurring, and severity can be judged by the snoring sound's audio volume, continuity, or discontinuity.

Sleep apnea greatly impacts the body, including the cardiovascular, cerebrovascular, respiratory, metabolic systems, etc. At present, there are two main treatment methods for snoring: wearing a continuous positive airway pressure (CPAP) or braces to stop snoring, or craniofacial or ENT surgery. However, the above-mentioned treatment methods are costly and must hear a certain amount of discomfort (a device in the oral cavity, surgical wound, etc.). In addition, there are many treatment devices for snoring on the market, such as medical beds with horizontal movement. Still, most of them have some defects, for example: affecting sleep, interference of electronic radiation waves, etc. Moreover, the medical bed that moves horizontally only functions as horizontal shakily. Although it can effectively improve snoring, for patients with other chronic diseases and symptoms, shaking cannot completely improve and solve the problem. Therefore, there are still deficiencies in conventional solutions for improving apnea and snoring, and how to improve the patient's snoring and apnea problems without affecting the quality of sleep has become a problem to be solved in the related field.

SUMMARY OF THE DISCLOSURE

The primary purpose of the present disclosure is to treat snoring in a way that does not affect sleep and does not invade the human body. The method and the device of the present disclosure are safe without incurring high costs, and also improve the problems in the conventional art. TO achieve the objective and effect, the present disclosure provides an Operating method of an anti-snoring rehabilitation device, including a starting step, a lifting step, a horizontal reciprocating step and an adjusting step. The anti-snoring rehabilitation device includes a folding mattress and a movable framework, and the folding mattress is disposed on top of the movable framework. In the starting step, the movable framework is electrically connected to an electric control screen used to drive the movable framework to horizontal reciprocate or fold, and the folding mattress simultaneously moves with the movable framework together. Lifting step; activating the electronic control screen to control part of the movable framework to perform multi-section folding and swinging; wherein the folding mattress includes a main control component including a detecting unit for monitoring the snoring volume, time, frequency and transmitting a control signal to a control substrate of the electric control screen; the control substrate converts the control signal and controls drives the movable framework to fold, and the folding mattress simultaneously moves with the movable framework together; wherein, the movable framework has a first support section, a second support section, a third support section and a fourth support section; the first support section, the second support section, the third support section and the fourth support section are connected with three pivot portions; wherein a lateral tilt angle of the first support section is from 0 to 40 degrees. Horizontal reciprocating step: after the lifting step, the movable framework further operates a reciprocating motor disposed under the movable framework to horizontal reciprocating move the movable framework, the reciprocating motion of the movable framework simultaneously drives the folding mattress to move backward and forward together. Adjusting step: the detecting unit continuously detects in the lifting step and horizontal reciprocating step and continuously transmits the control signal to the control substrate, and the control substrate adjusts the movable framework according to the control signal.

BRIEF DESCRIPTION OF THE DRAWINGS

The described embodiments may be better understood by reference tee the following, description and the accompanying drawings in which.

DETAILED DESCRIPTION OF THE EXEMPLARY EMBODIMENTS

The construction and method of operation of the present disclosure, together with additional objects and advantages thereof will be best understood from the following description of one or more embodiment(s) when read in connection with the accompanying drawings.

Referring to FIGS. 1-12, the present disclosure provides an operating method of an anti-snoring rehabilitation device, including a starting step S1, a lifting step S2, a horizontal reciprocating step S3 and an adjusting step S4. Starting step S1: providing an anti-snoring rehabilitation device 10 for a patient/user lying on it; the anti-snoring rehabilitation device 10 includes a folding mattress 1 and a movable framework 2. The folding mattress 1 is disposed on the top of the movable framework 2, the movable framework 2 is wire/wireless electrically connected to an electric control screen 3 (for example, remote control) used to drive the movable framework 2 to horizontal reciprocate or fold, and the folding mattress 1 simultaneously move with the movable framework. 2 together. Lifting step S2: activating the electronic control screen 3 to control part of the movable framework 2 to perform multi-sections folding.

Figure 1:
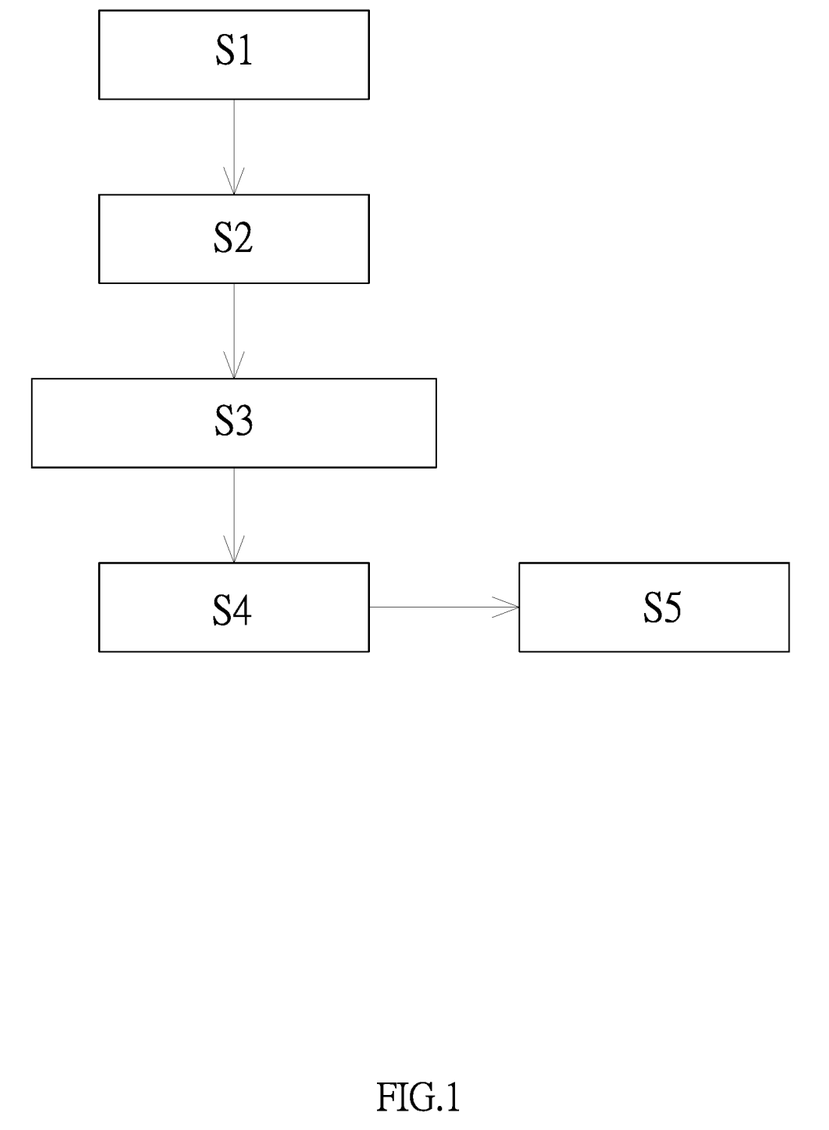
FIG. 1 is a block schematic diagram of the step of the present disclosure.
Figure 2:
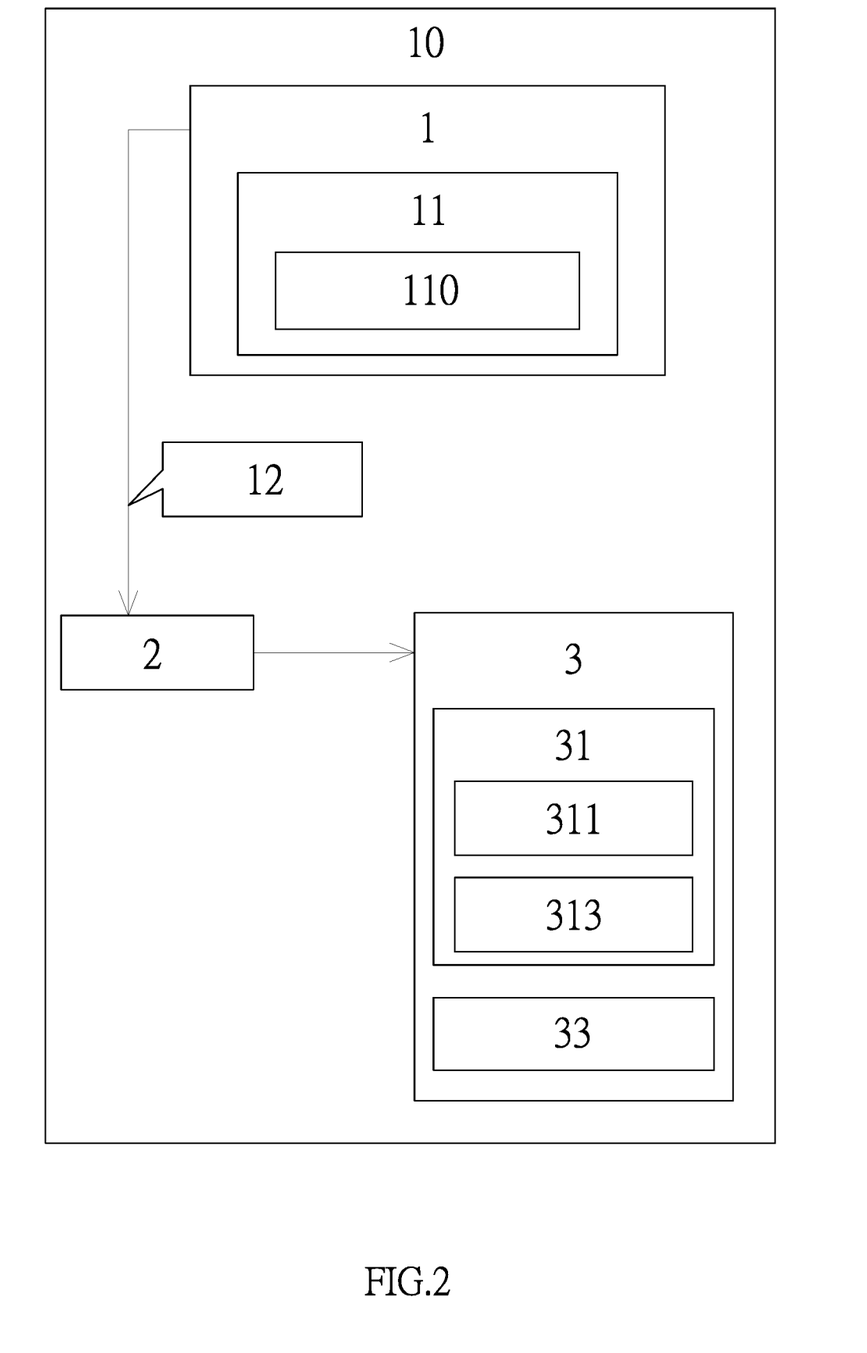
FIG. 2 is a block schematic diagram of the structure of the present disclosure.

Further, the folding mattress 1 includes a main control component 11 including a detecting unit 110 for monitoring the snoring volume, time and frequency, and transmitting a control signal 12 to a control substrate 31 of the electric control screen 3. The control substrate converts the control signal 12 and controls/drives the movable framework 2 to fold, and the folding mattress 1 simultaneously moves with the movable framework 2 together. Furthermore, the movable framework 2 has a first support section 21 corresponding to the head, a second support section 22 corresponding to the buttocks, a third support section 23 corresponding to the thigh and a fourth support section 24 corresponding to the calf, the four support sections (21-24) are connected by three pivot portions 25. The pivot portion 25 between the first support section 21 and the second support section 22 is regarded as the axis for folding, and a lateral tilt angle of the first support section is from 0 to 40 degrees. Horizontal reciprocating step S3: after the lifting step S2, the movable, framework 2 further operates a reciprocating motor 26 disposed under the movable framework 2 to horizontal reciprocating move the movable framework 2, the reciprocating motion of the movable framework 2 simultaneously drives the folding mattress 1 to move backward and forward together. Adjusting step S4; the detecting unit 110 continuously detects in the lifting step S2 and horizontal reciprocating step S3, and continuously transmits control signal 12 to the control substrate 31, and the control substrate 31 fine-adjusts the movable framework 2 according to the control signal 12.

Specifically, sleep apnea is caused by a blockage of the airway, usually when the soft tissue in the rear of the throat collapses during sleep. Snoring is caused by the flapping and vibration of relaxed tissues of the mouth and throat as the patient inhales air. This device of the present disclosure is provided to reduce snoring.

The patient sleeps on the folding mattress 1 of the anti-snoring rehabilitation device 10 in a belly-up position. Operating, the device via electronic control screen 3 to control the movable framework 2. Once the patient starts snoring, the main control component 11 or the folding mattress 1 measures the volume, time period, and frequency of snoring and transmits the control signal 12 to the control substrate 31 of the electronic control screen 3. The control substrate 31 analog/digital converts the control signal 12 and adjusts the movable framework 2 by operating a reciprocating motor 26. Firstly, according to the control signal 12, drive the movable framework 2 to lift and fold. The first, second, third and fourth support sections (21, 22, 23, 24) are adjusted according to the patient's body type, and the folding mattress 1 is simultaneously adjusted with the movable framework 2. The adjustments of these first, second, third and fourth support sections (21, 22, 23, 24) are designed with pivot settings to adjust the lateral tilt angle. The lateral tilt angle of the first and fourth support sections of the movable framework 2 is 35 degrees ±10 degrees, During the adjustment of the movable framework 2, the patient's position is modified allo allowing the internal organs of the patient to be moved or shook with the body so that the airflow in the internal organs can be released. Meanwhile, the soft tissue in the rear of the throat switches position to help create a smoother airway, ultimately reducing, breathing noise.

Figure 9:
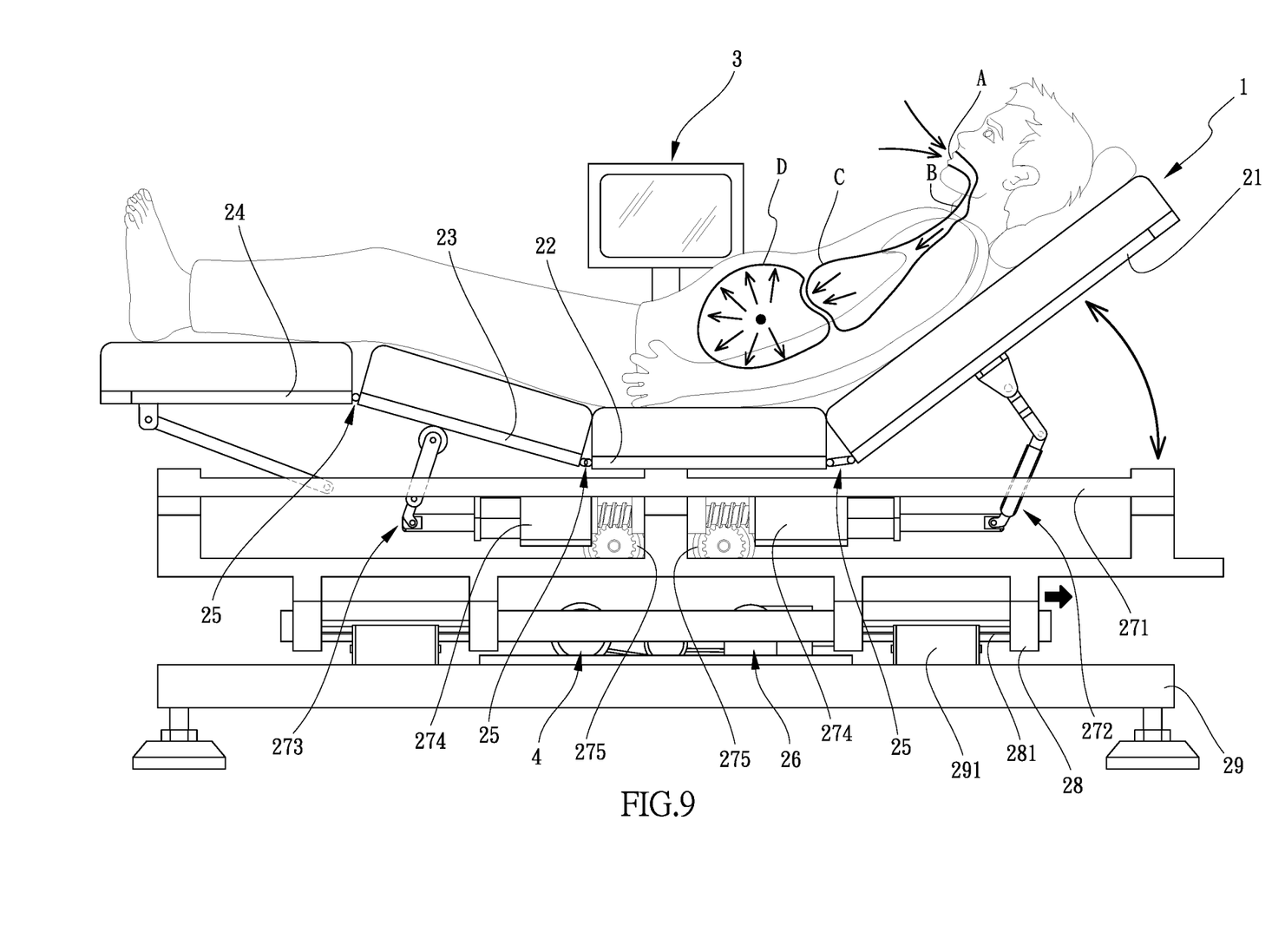
FIG. 9 is a side schematic view of the movement of the movable framework that drives the folding mattress to move in the direction indicated by the arrow and the airflow in the internal organs.
Figure 10:
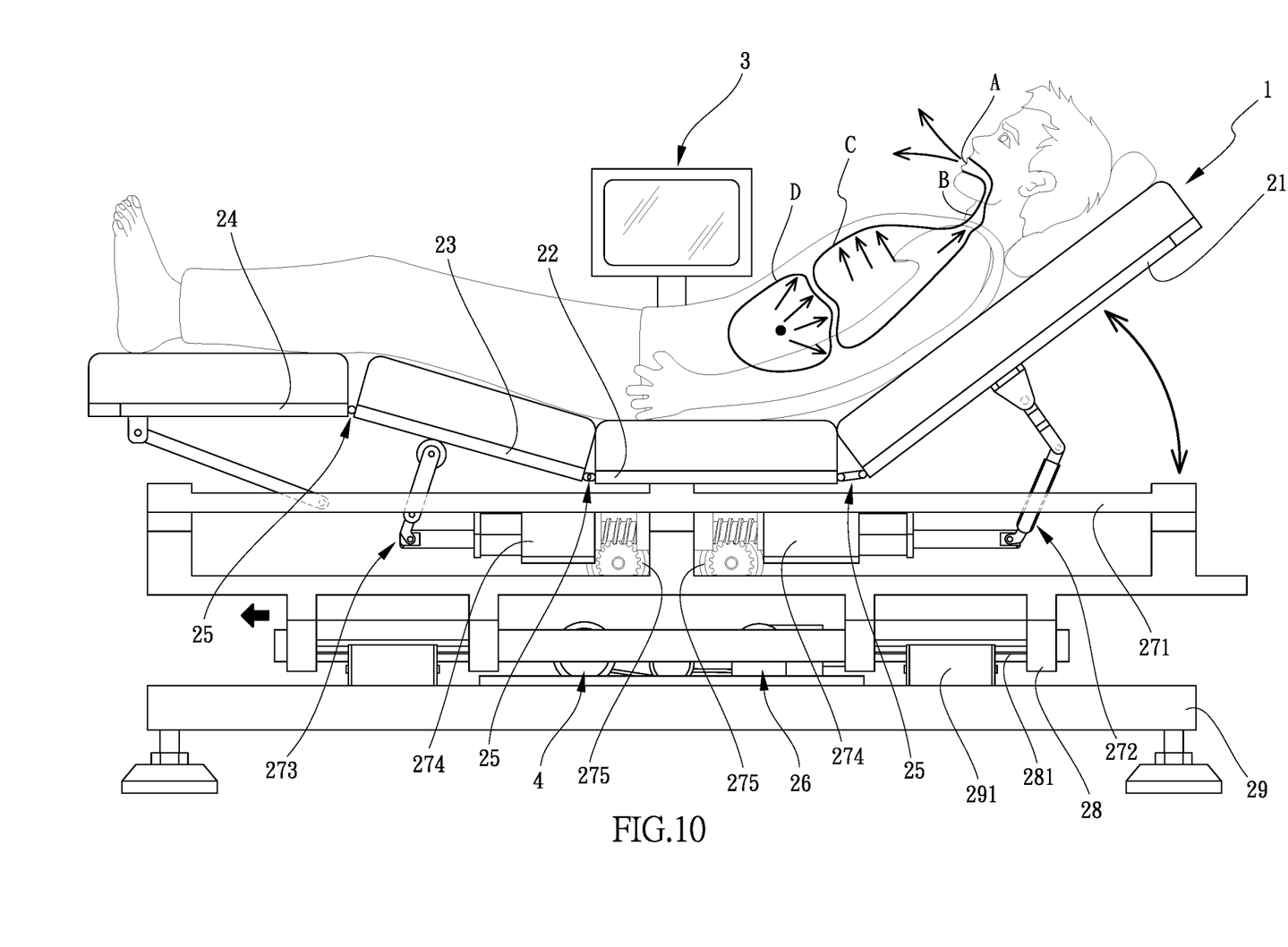
FIG. 10 is a side schematic view of the movement of the movable framework that drives the folding mattress to move in the direction indicated by the arrow and the airflow in the internal organs.

After raising adjustments of the first, second, third and the fourth support sections (21, 22, 23, 24), the control substrate 31 modifies the movable framework 2 by controlling the reciprocating motor 26. The frequency of the horizontal reciprocating movement of the movable framework 2 is 3.0-6.0 Hz. The movement of the horizontal reciprocation can be read in conjunction with FIGS. 9 and 10. The patient's internal organs' positions are adjusted after the lilting step, and the horizontal reciprocation allows the patient's lungs to be repeatedly compressed and stretched. When the lungs are compressed, the gravity leads the diaphragm and abdominal cavity to change position in an oppositional direction from the movement of the movable framework 2, so that the positive pressure is generated in the lungs and the air in the lungs is released from the mouth through the throat (as shown in FIG. 10, the black dot in the abdominal cavity is the center). Similarly, when the lungs are stretched, the diaphragm and abdominal cavity move towards the movable framework 2 due to the downward gravity force and change position in the opposite direction to generate the negative pressure in the lungs, so that it allows air to enter the lungs from the mouth through the throat (as shown in FIG. 9). By this way, the position where the snoring sound is caused by the collapse of the throat is opened, and the air can be prevented from being blocked at the collapsed place, so that the generation of snoring sound can be completely eliminated.

Figure 3:
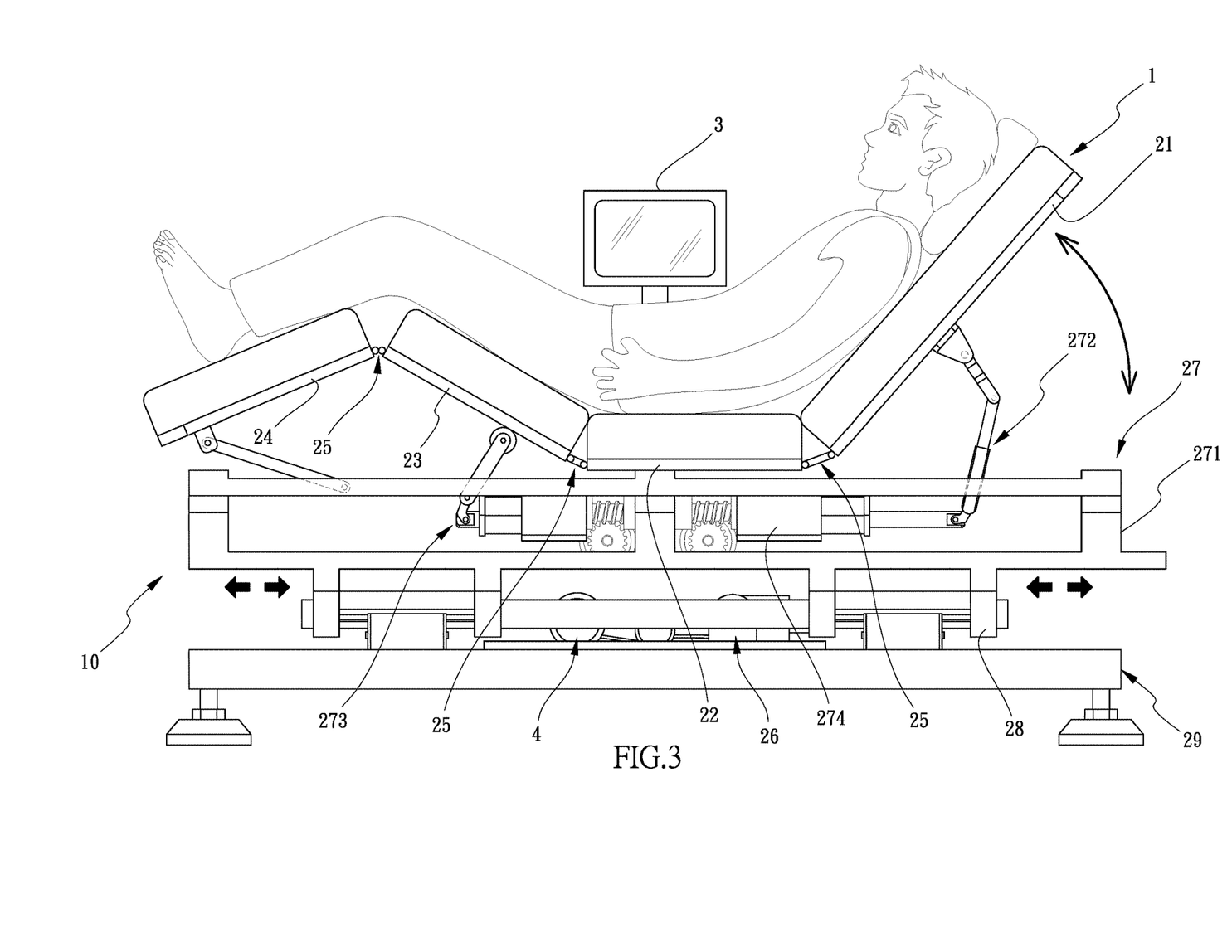
FIG. 3 is a schematic view of lifting the first support section, the third support section and the fourth support section of the folding mattress of the present disclosure for performing cardiopulmonary resuscitation.

In the above treatment process, the detecting unit 110 located in the folding mattress 1 will continuously monitor the patient to prevent the change of position during treatment or circumstances that may change the decibel of the snoring volume, time, frequency, etc. Therefore, with continual monitoring of the detecting unit 110, the adjustment of the movable framework 2 is accurate and precise, so the patient can avoid snoring in any position during sleep. The device of the present disclosure not only benefits the sleep quality of others but, more importantly, prevents sleep apnea for the user during sleep. In brief, under continual monitoring of patient-snoring of the detecting unit 110, the control signal 12 is transmitted to the control substrate 31 of the electronic control screen 3 to control the lifting of the first, second, third and the fourth support sections (21, 22, 23, 24), so as to fold the folding, mattress 1. The lateral tilt angle of the first, second, third and fourth support sections (21, 22, 23, 24) decreases as snore-volume decreases and for the reciprocating motor 26. When the snore-volume decreases, the frequency of the horizontal reciprocating support framework also decreases. This allows the patients to adapt to their angle and reciprocation speed over a longer period of time. In addition to snoring prevention, this device has an additional feature to provide a certain level of CPR function. During a medical emergency when no staff is present to perform CPR, the anti-snoring rehabilitation device 10, the third support section 23, and the fourth support section 24 are utilized to create an exaggerated pivot swing, curling the patient into a fetal position to provide a squeeze or internal organs. At the same time, the operation of the reciprocating motor 26 and the central control screw set 274 allow the anti-snoring rehabilitation device 10 to move horizontally, so that the patient's heart can be squeezed and expanded, contracted, and relaxed repeatedly with other body organs, which provides a proper massage of the heart and beneficial emergency treatment, as shown in FIG. 3.

Generally, for patients undergoing sleep apnea treatment, when they are in medical institutions, the conditions of the patients being treated are different, and each rehabilitation treatment must be readjusted, which is time-consuming for therapists and rehabilitation practitioners. Thus, the control substrate of the electric control screen of the present disclosure includes a recording unit 311. After adjusting step S4, a memory step S5 can be provided. When the patient is undergoing treatment and rehabilitation, the height position and lateral tilt angle of the movable framework 2 align with the current patient's needs. The recording unit 311 records the last position of the movable framework 2. The therapist and rehabilitator only need to enter corresponding patient information in the control screen 3 to access the information and adjust the movable framework 2 to the previous position directly and quickly. It saves the process of repeated fine-tuning, which is convenient also time-saving. Referring to FIG. 2 (an external mobile device can be connected to the record file of the present disclosure, such as a computer (not shown in the figures).

As shown in FIG. 2, in order to avoid any emergency during sleep and the patient cannot suspend the device in time, or other external factors that cause the patient's snoring to change during the treatment and rehabilitation process, or an abnormality or the like occurs during the detection process by the detecting unit 110, the control substrate 31 further includes an alert unit 313, and the electric control screen includes a buzzer 33 (or beeper) to alert the therapist, physiotherapist, or patient. When the alert unit 313 detects the control signal 12 of the control substrate 31 is abnormal, or the control signal 12 is abnormal when transmitted to the control substrate 31, the alert unit 313 operates and controls the buzzer 33 to generate audio sound. The audio sound reminds the relevant personnel and the patient that there is a problem or abnormality in the detection or transmission of the control signal 12, which must be solved and improved to avoid the wrong control signal that drives the movable framework 2 to perform improper adjustment and action.

Figure 4:
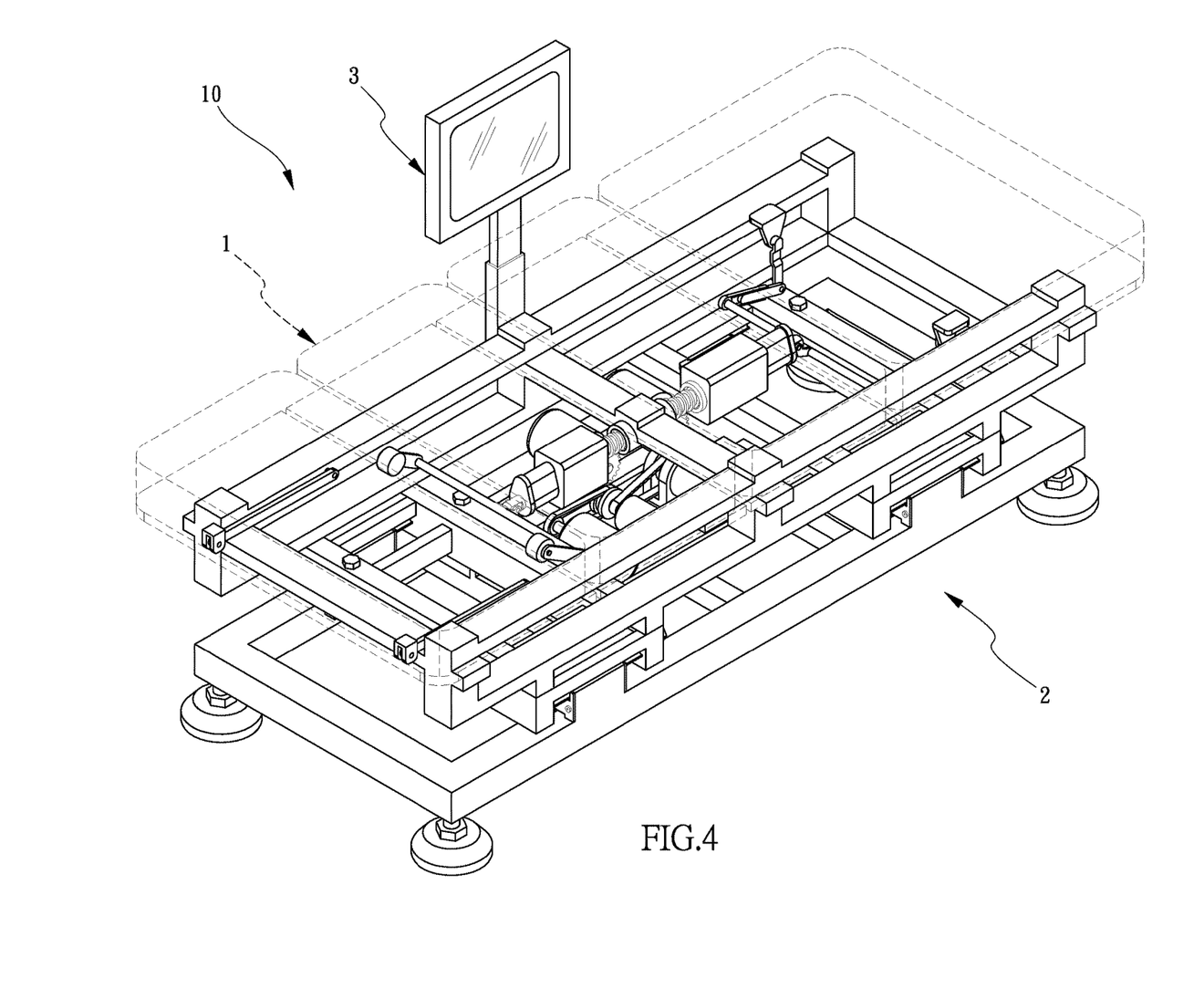
FIG. 4 is a perspective schematic view of the present disclosure.
Figure 5:
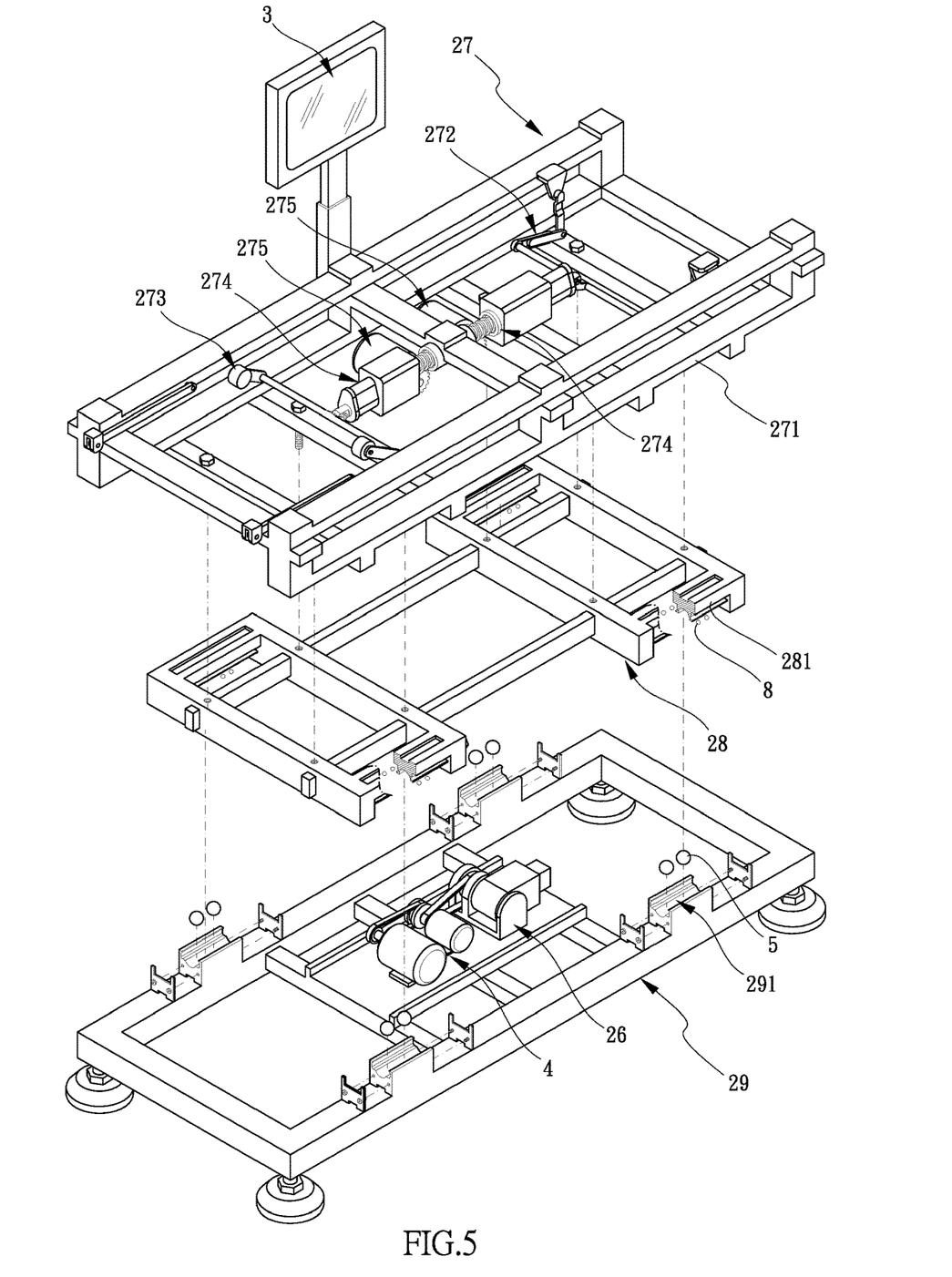
FIG. 5 is an exploded perspective schematic view of FIG. 4.
Figure 6:
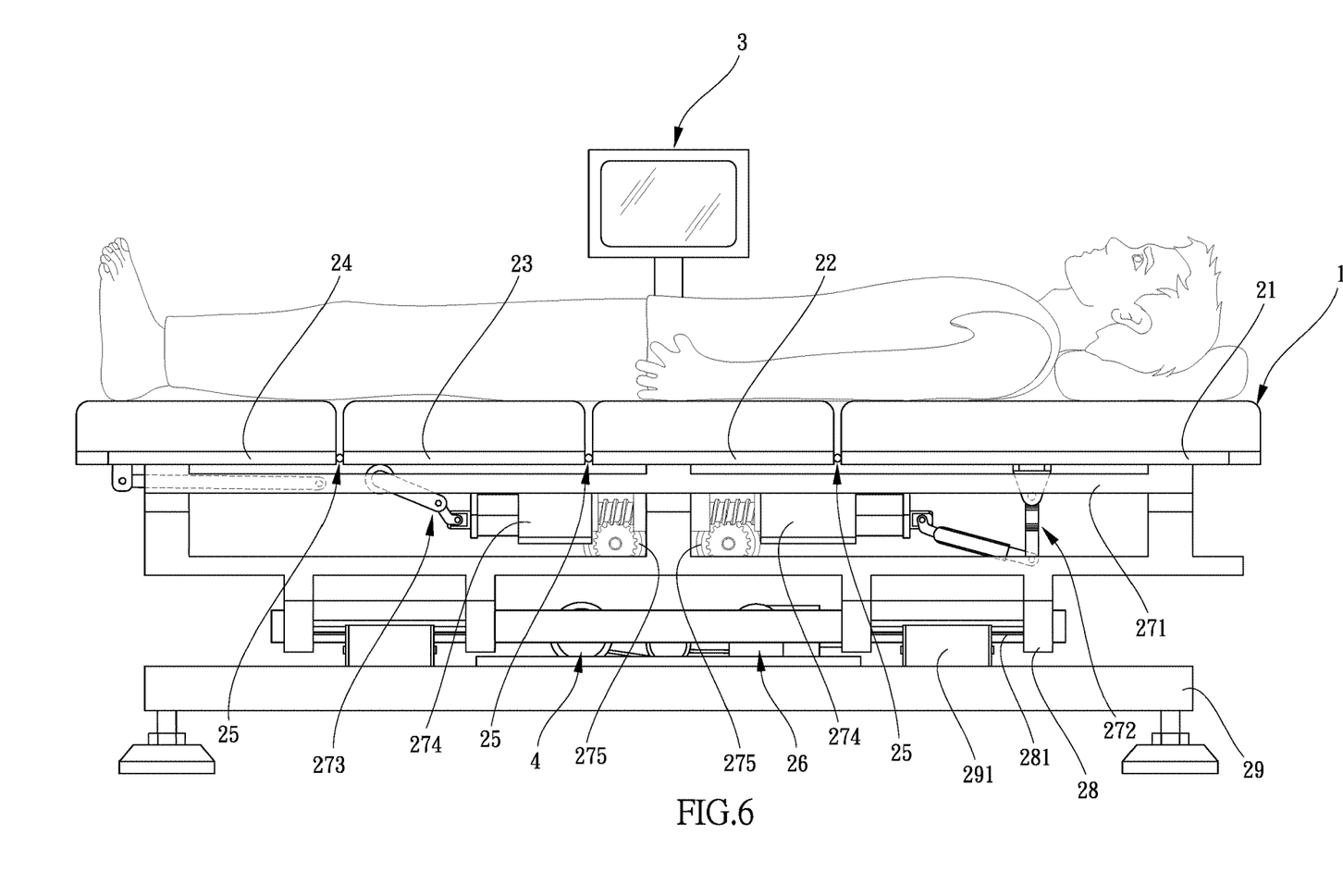
FIG. 6 is a side schematic view of FIG. 4 without adjustment.
Figure 7:
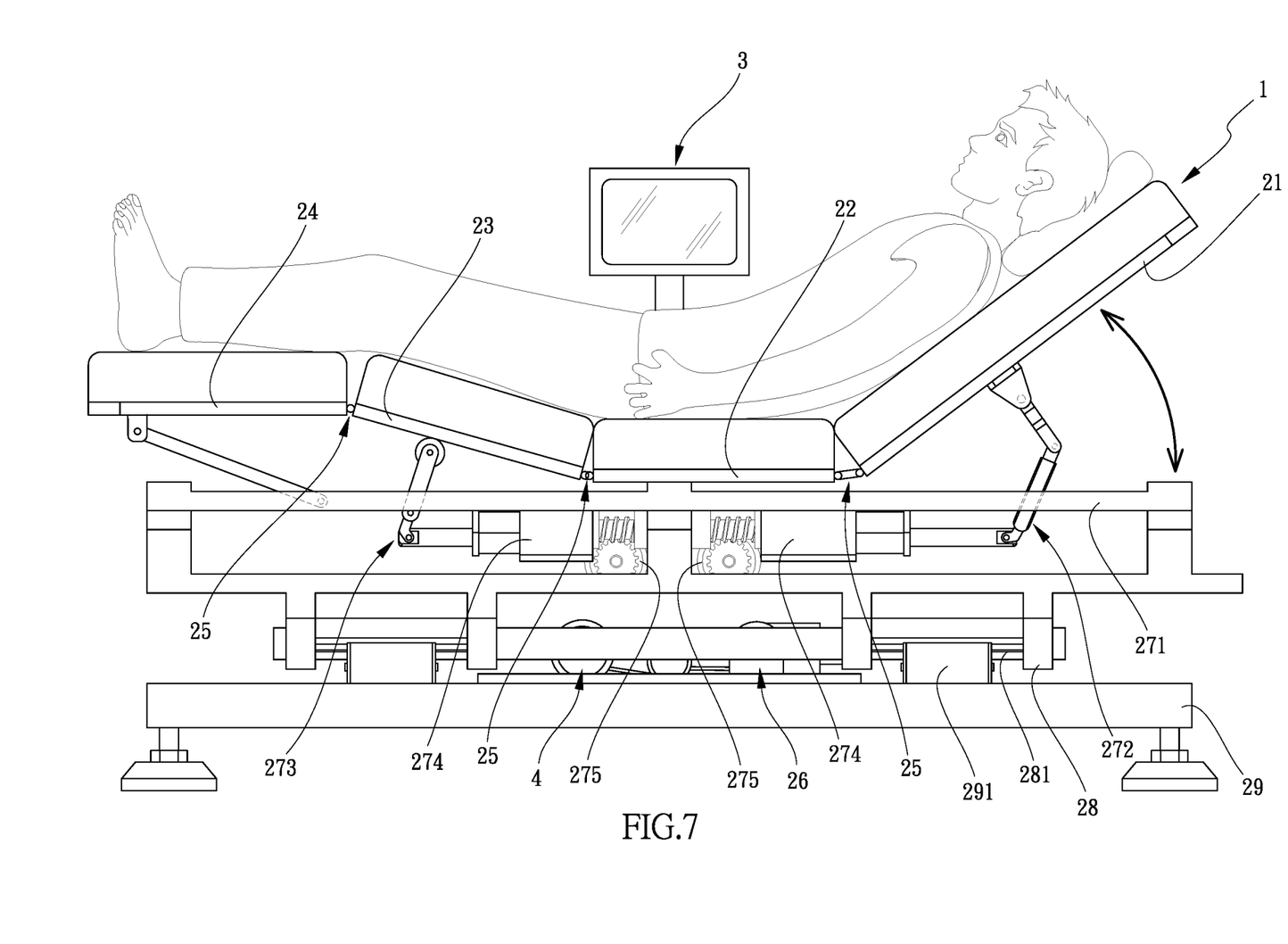
FIG. 7 is a side schematic view of the movement of the movable framework driving, the folding mattress.

In addition, the structural features of the movable framework 2, as shown in FIG. 4 and FIG. 5, the movable framework 2 includes an upper framework set 27, an actuating frame set 28 and a lower framework set 29. The outer periphery of the lower framework set 29 is a square outer frame, and the top surface of the outer frame of the lower framework set 29 is provided with a plurality of track members 291, each track member 291 is spaced apart with distance (as shown in FIG. 4). A lower driving motor 4 is electrically connected to and provides electricity to the electric control screen 3 and the reciprocating motor 26. The lower driving motor 4 is located between the upper framework set 27 and the actuating frame set 28. The reciprocating motor 26 is located at the middle position of the lower framework set 29. The actuating frame set 28 is located on the upper side of the lower framework set 29. The actuating frame set 28 has a plurality of sliding members 281 corresponding to the plurality of track members 291 (as shown in FIG. 5), and a plurality of spheres 5 are covered between each track me fiber 291 and each sliding member 281 (two spheres 5 are shown in FIG. 51. The spheres 5 increases the smoothness of horizontal reciprocating movement of the plurality of sliding member 281 and the plurality of track pieces 291. The upper framework set 27 is disposed can the actuating frame set 28, the upper framework set 27 includes an upper frame 271, a first driving set 272, a second driving set 273 and a central control screw set 274. The central control screw set 274 includes at least one upper driving motor 275 wire/wireless electrically connected to the control substrate 31 and controlling the first driving set 272 and the second driving set 273 to telescopic operation. In detail, the first driving set 272 is disposed on one side of the upper frame 271, and the second driving set 273 is disposed on the other side of the upper frame 271, so that the first driving set 272 and the second driving set 273 are disposed in the opposite direction. The central control screw set 274 is disposed on the middle side of the upper frame 271 and connected with the first driving set 272 and the second driving set 273. The central control screw set 274 is a set of mechanisms with double-ended electric screws, the two ends of which can be extended/shortened. The central control screw set 274 is driven by the upper driving motors 275 to drive the first driving set 272, and the second driving set 273 lift up and down. The first, second, third, and fourth support sections (21, 22, 23, 24) of the movable framework 2 are formed by concave and foldable plates, and a pivot portion 25 is provided between the plates. The first, second, third, and fourth support sections (21, 22, 23, 24) and the pivot portion 25 are disposed on the upper framework set 27. The first driving set 272 corresponds to the first support section 21, and the second driving set 273 is roller-typed against and rolling between the bottom surface of the third and fourth supporting sections (23, 24). The first driving set 272 is used to support the upper body of the patient, as shown in FIG. 7. Further, the first, second, third, and fourth support sections (21, 22, 23, 24 and the folding mattress 1 can be formed in one piece or separate structures.

Figure 8:
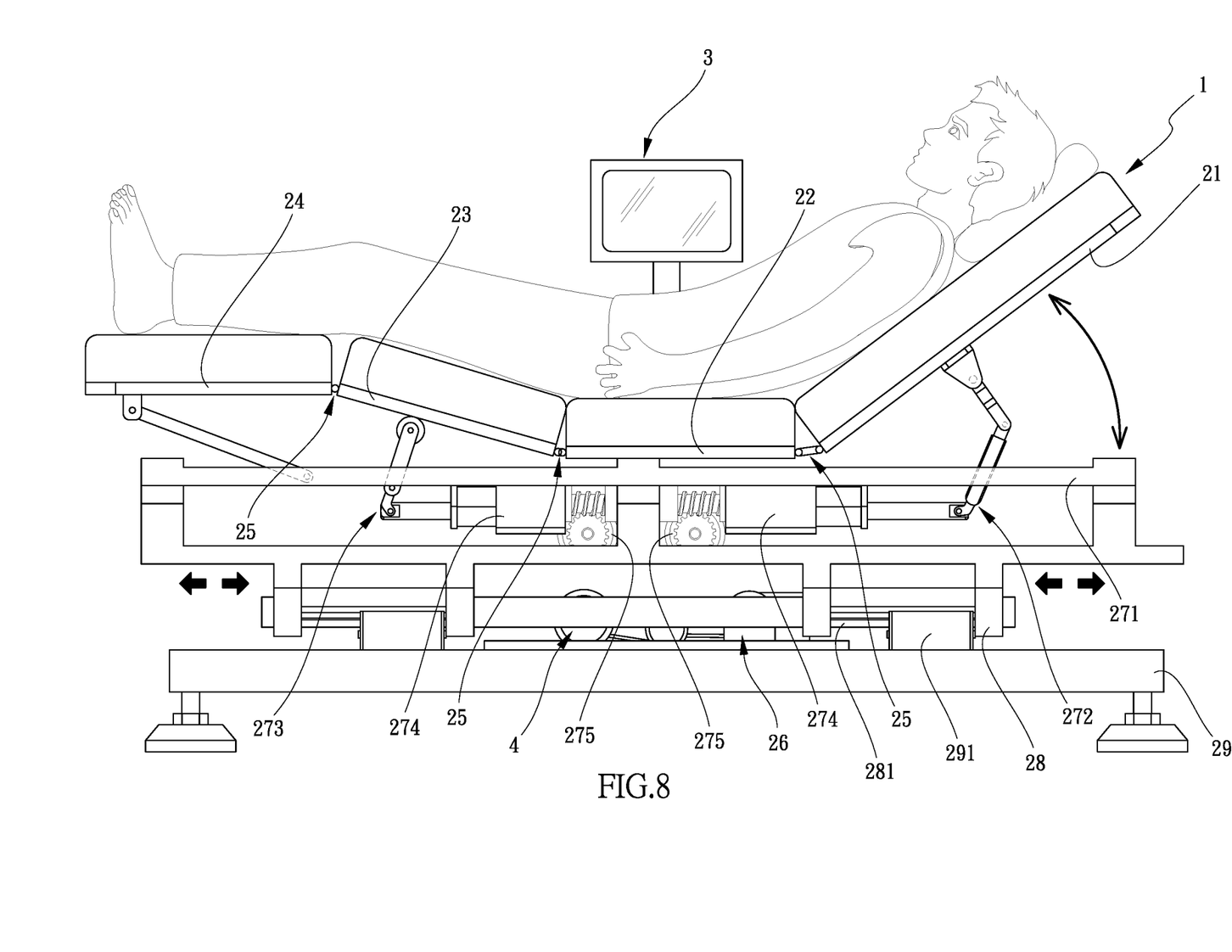
FIG. 8 is a side schematic view of the movable framework of the present disclosure horizontal move backward and forward.
Figure 11:
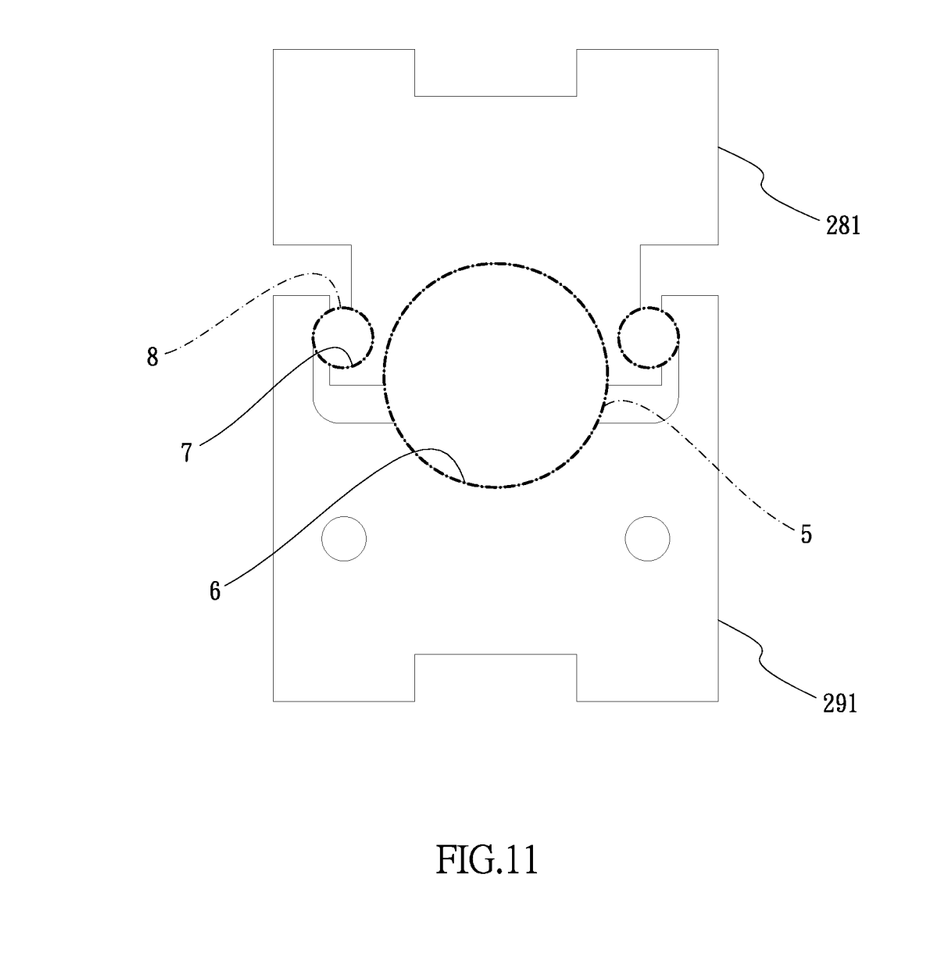
FIG. 11 is a sectional schematic view of line XI-XI of FIG. 4 in the operation of the present disclosure.

Finally, in order to enhance the smoothness of sliding between each track member 291 and each sliding member 281, the sliding connections between each track member 291 and each sliding member 281 are further divided into a main track 6 and two side tracks 7, the main track 6 covers the sphere 5, and the two side tracks covers a plurality of auxiliary balls 8. Each auxiliary hall 8 and each sphere 5 can provide better smoothness when each sliding member 281 horizontally reciprocates relative to each rail member 291. Further, the arrangement of each auxiliary hall 8 is to balance the movement of each sliding member 281 in the track of each track member 291, so as to avoid inclining and affecting the horizontal reciprocating movement or the upper framework set 27, as shown in FIGS. 5, 8 and 11.

In conclusion, the treatment and rehabilitation of snoring can be carried out through the method of the present disclosure. By virtue of the actuating frame set 28 of the movable framework 2, each pivot portion 25 between the folding mattress 1 and the first, second, third and fourth support sections (21, 22, 23, 24) of the movable framework 2 can be folded and pivoted, so that the first, second, third and fourth support sections (21, 22, 23, 24) can support different body part of the patient, so that move and adjust the position of the organs to avoid snoring. Further, the upper framework set 27 is driven to move backward and forward horizontally by the actuating frame set 28, and the lungs can interactive to operate positive and negative pressure through the shaking of the movement to achieve air intake and discharge, and also overcome the problem of collapsing throat. Moreover, in the lifting step S2, the first support section 21 can not only move to the position simply, but also clap continuously, so that the first support section 21 can perform percussion to the patient's back and dissolve phlegm by the vibration of the percussion and avoid affecting the quality of sleep.

What is claimed is:

1. An operating method of an anti-snoring rehabilitation device, comprising:

starting step; providing an anti-snoring rehabilitation device for a user lying on it; wherein the anti-snoring rehabilitation device includes a folding mattress and a movable framework, the folding mattress disposed on the top of the movable framework; wherein the movable framework is electrically connected to an electric control screen used to drive the movable framework to horizontal reciprocate or fold, and the folding mattress simultaneously move with the movable framework together;

lifting step: activating the electronic control screen to control part of the movable framework to perform multi-section folding; wherein, the folding mattress includes a main control component including a detecting unit for monitoring the snoring volume, time, frequency and transmitting a control signal to a control substrate of the electric control screen; wherein the control substrate converts the control signal and controls the movable framework to fold, and the folding mattress simultaneously move with the movable framework together; wherein, the movable framework has a first support section, a second support section, a third support section and a fourth support section; the first support section, the second support section, the third support section and the fourth support section are connected with three pivot portions; wherein a lateral tilt angle of the first support section is from 0 to 40 degrees;

horizontal reciprocating step: after the lifting step, the movable framework operating a reciprocating motor disposed under the movable framework to horizontal reciprocating move the movable framework, and the reciprocating motion of the movable framework simultaneously driving the folding mattress to move backward and forward together; and adjusting step: the detecting unit continuously detecting in the lifting step and horizontal reciprocating step, and continuously transmitting the control signal to the control substrate, and the control substrate adjusting the movable framework according to the control signal;

the movable framework includes an upper framework set, an actuating frame set and a lower framework set;

wherein the top surface of the lower framework set has a plurality of track members spaced apart, and a lower driving motor electrically connected to the electronic control screen and the reciprocating motor;

wherein the reciprocating motor is disposed at the middle side of the lower framework set, and the actuating frame set is disposed on the top of the lower framework set: wherein the actuating frame set has a plurality of sliding members corresponding to the plurality of track members, and each of a plurality of spheres is covered by each sliding member and track member;

wherein the upper framework set is disposed on the actuating frame set. the upper framework set includes an upper frame, a first driving set, a second driving set and a central control screw set: wherein, the first driving set is disposed on one side of the upper frame, and the second driving set is disposed on the other side of the upper frame;

wherein, the central control screw set is disposed on the middle side of the upper frame and connected with the first driving set and the second driving set;

wherein, the central control screw set includes at least one upper driving motor electrically connected to the control substrate and controlling the first driving set and the second driving set to telescopic operation;

wherein the central control screw set is connected to the lower driving motor;

wherein the telescopic operation of the first driving set and the second driving set concave fold the folding mattress and the movable framework.

2. The operating method of an anti-snoring rehabilitation device according to claim 1, further including a memory step; wherein the control substrate of the electric control screen includes a recording unit, the recording unit records the last folding angle and position of the movable framework for subsequent use.

3. The operating method of an anti-snoring rehabilitation device according to claim 1, wherein the control substrate includes an alert unit, and the electric control screen includes a buzzer; wherein, the alert unit detects the control signal of the control substrate, when the control signal fails to be transmitted or detected, the alert unit operates and controls the buzzer to generate audio sound.

4. The operating method of an anti-snoring rehabilitation device according to claim 1, wherein each track member and each sliding member fittingly engaged to be a main track and two sidetracks; wherein the main track covers the sphere, and the two side tracks cover a plurality of auxiliary balls.

* * * * *